(12) United States Patent
Terstappen et al.

(10) Patent No.: US 6,790,366 B2
(45) Date of Patent: Sep. 14, 2004

(54) MAGNETIC SEPARATION APPARATUS AND METHODS

(75) Inventors: Leon W. M. M. Terstappen, Huntingdon Valley, PA (US); Gerald Dolan, Huntingdon Valley, PA (US)

(73) Assignee: Immunivest Corporation, Wilmington, DE (US)

( * ) Notice: Subject to any disclaimer, the term of this patent is extended or adjusted under 35 U.S.C. 154(b) by 31 days.

(21) Appl. No.: 10/602,979

(22) Filed: Jun. 24, 2003

(65) Prior Publication Data

US 2004/0004043 A1 Jan. 8, 2004

Related U.S. Application Data

(60) Division of application No. 09/856,672, filed as application No. PCT/US99/28231 on Nov. 30, 1999, which is a continuation-in-part of application No. 09/201,603, filed on Nov. 30, 1998, now Pat. No. 6,136,182, which is a continuation-in-part of application No. 08/867,009, filed on Jun. 2, 1997, now Pat. No. 5,985,153.

(60) Provisional application No. 60/019,282, filed on Jun. 7, 1996, and provisional application No. 60/030,436, filed on Nov. 5, 1996.

(51) Int. Cl.$^7$ .................. B01D 35/06; G01N 33/533
(52) U.S. Cl. .................. 210/695; 210/94; 210/222; 436/177; 436/526; 435/7.2; 209/213; 209/214; 209/223.1
(58) Field of Search .................. 210/695, 94, 222; 436/177, 526; 435/7.2; 209/213, 214, 223.1

(56) References Cited

U.S. PATENT DOCUMENTS

| | | |
|---|---|---|
| 4,729,949 A | 3/1988 | Weinreb |
| 4,735,504 A | 4/1988 | Tycko |
| 4,989,978 A | 2/1991 | Groner |
| 5,030,560 A | 7/1991 | Sinor |

(List continued on next page.)

FOREIGN PATENT DOCUMENTS

| | | |
|---|---|---|
| WO | WO 94/11078 | 5/1994 |
| WO | WO 96/26782 | 9/1996 |

OTHER PUBLICATIONS

Chen et al., "Automated Enumeration of CD34+ Cells in Peripheral Blood and Bone Marrow", J. of Hematotherapy; 3:3–13 (1994).

(List continued on next page.)

Primary Examiner—David Reifsnyder
(74) Attorney, Agent, or Firm—Joseph F. Aceto; James Wilcox; Immunicon Corp

(57) ABSTRACT

Apparatuses and methods for separating, immobilizing, and quantifying biological substances from within a fluid medium. Biological substances are observed by employing a vessel (6) having a chamber therein, the vessel comprising a transparent collection wall (5). A high internal gradient magnetic capture structure may be on the transparent collection wall (5), magnets (3) create an externally-applied force for transporting magnetically responsive material toward the transparent collection wall (5). The magnetic capture structure comprises a plurality of ferromagnetic members and has a uniform or non-uniform spacing between adjacent members. There may be electrical conductor means supported on the transparent collection wall (5) for enabling electrical manipulation of the biological substances. The chamber has one compartment or a plurality of compartments with differing heights. The chamber may include a porous wall. The invention is also useful in conducting quantitative analysis and sample preparation in conjunction with automated cell enumeration techniques.

6 Claims, 10 Drawing Sheets

U.S. PATENT DOCUMENTS

| | | | |
|---|---|---|---|
| 5,053,344 A | 10/1991 | Zborowski |
| 5,089,128 A | 2/1992 | Garaschenko |
| 5,200,084 A | 4/1993 | Liberti |
| 5,340,749 A | 8/1994 | Fugiwara |
| 5,375,606 A | 12/1994 | Slezak |
| 5,411,863 A | 5/1995 | Miltenyi |
| 5,428,451 A | 6/1995 | Lea |
| 5,451,525 A | 9/1995 | Shenkin |
| 5,466,574 A | 11/1995 | Liberti |
| 5,494,831 A | 2/1996 | Kindler |
| 5,498,550 A | 3/1996 | Fujiwara |
| 5,541,072 A | 7/1996 | Wang |
| 5,985,153 A | 11/1999 | Dolan |
| 6,136,182 A | 10/2000 | Dolan |

OTHER PUBLICATIONS deGroth et al., "The Cytodisk: A Cytometer Based Upon a New Principle of Cell Alignment", Cytometry; 6:226–233 (1995).

Kamentsky et al., "Microscope–Based Multiparameter Laser Scanning Cytometer Yielding Data Comparable to Flow Cytometry Data", Cytometry; 12:381–387 (1991).

Stewart, et al., "Quantitation of Cell Concentration Using the Flow Cytometer", Cytometry; 2:238–243 (1982).

Takayasu et al., "HGMS Studies of Blood Cell Behavior in Plasma", IEEE Transactions of Magnetics, 18:1520–1522 (1982).

Takayasu et al., "High Gradient Magnetic Separation II. Single Wire Studies of Shale Oils", IEEE Transactions on Magnetics; 18:1695–1697 (1982).

Zwerner et al., "A Whole Blood Alternative to Traditional Methods for CD4+ T Lymphocyte Determine" J. of Acquired Immune Deficiency Syndromes and Human Retrovirology; 14:31–34 (1997).

Ahn, et al., "A Fully Integrated Micromachined Magnetic Particle Manipulator and Separator", Proc. Workshop on Micro Electro Mechanical System IEEE, ISBN: 0–7803–1834–X, Jan. 25–28, 1994, pp. 91–96.

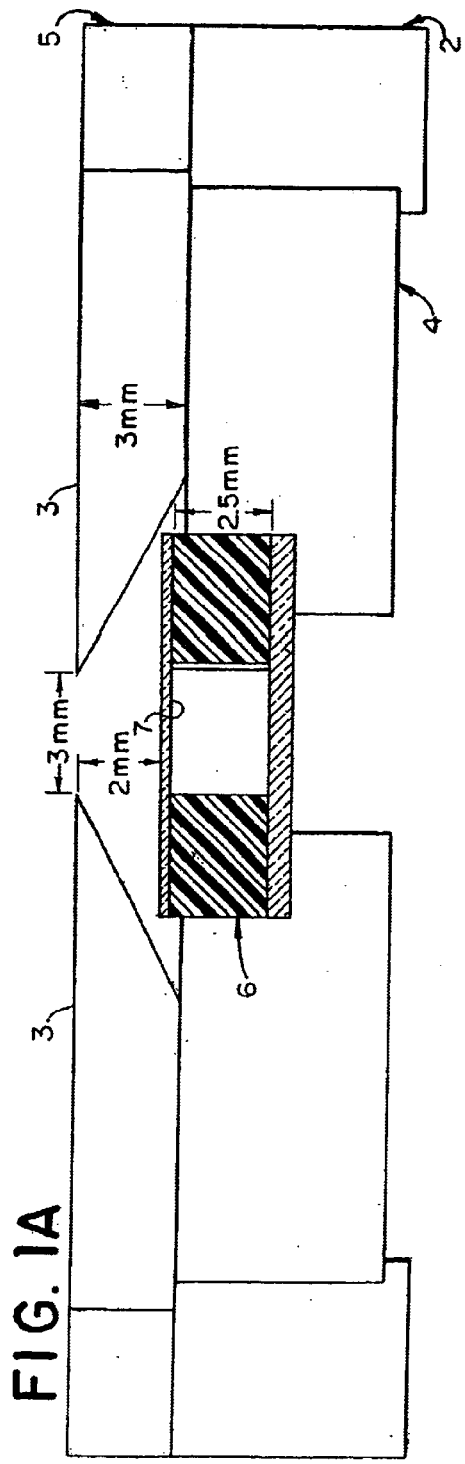
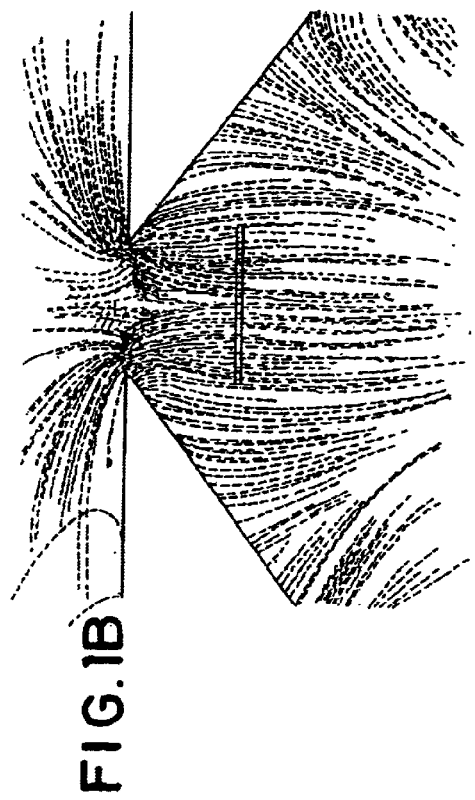
FIG. 1A
FIG. 1B

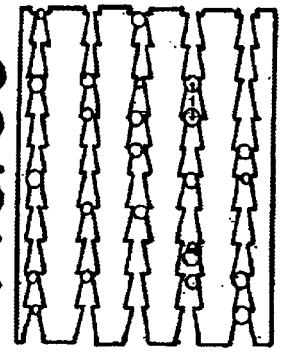
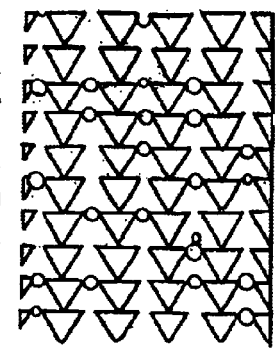
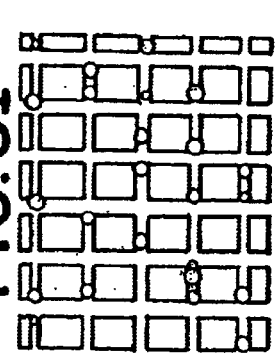
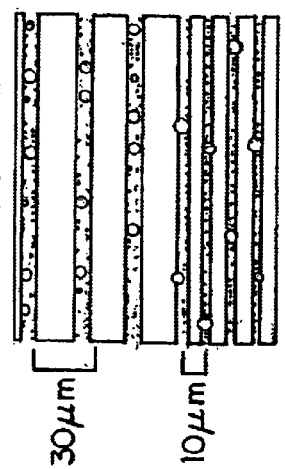
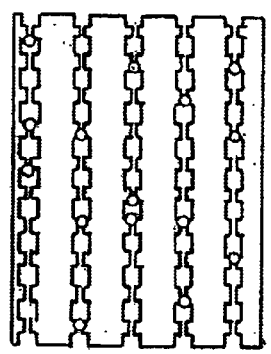
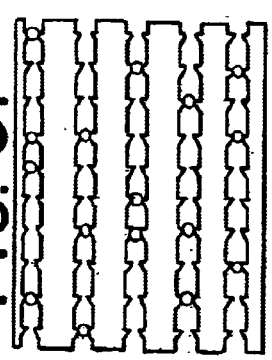
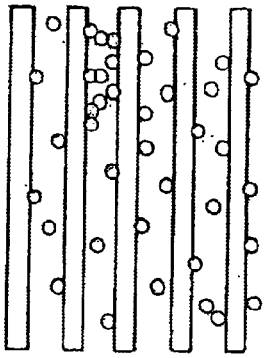
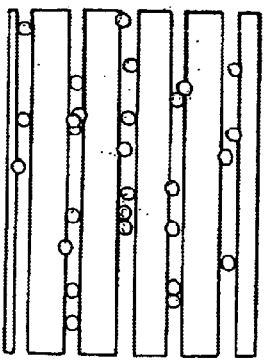
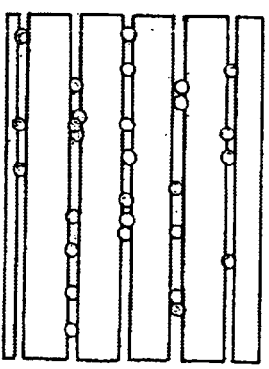

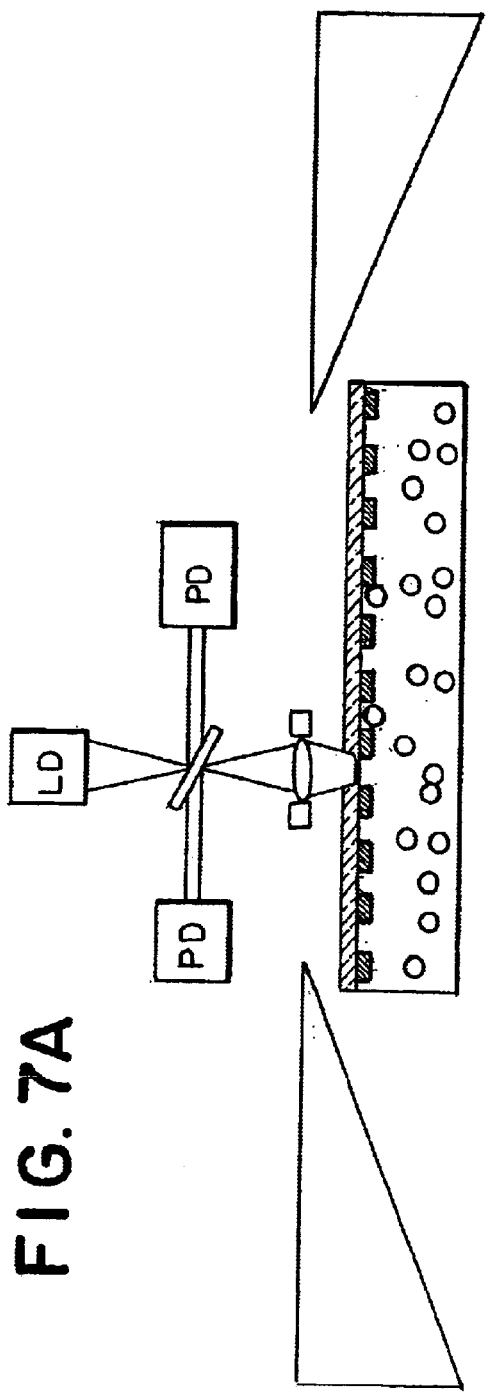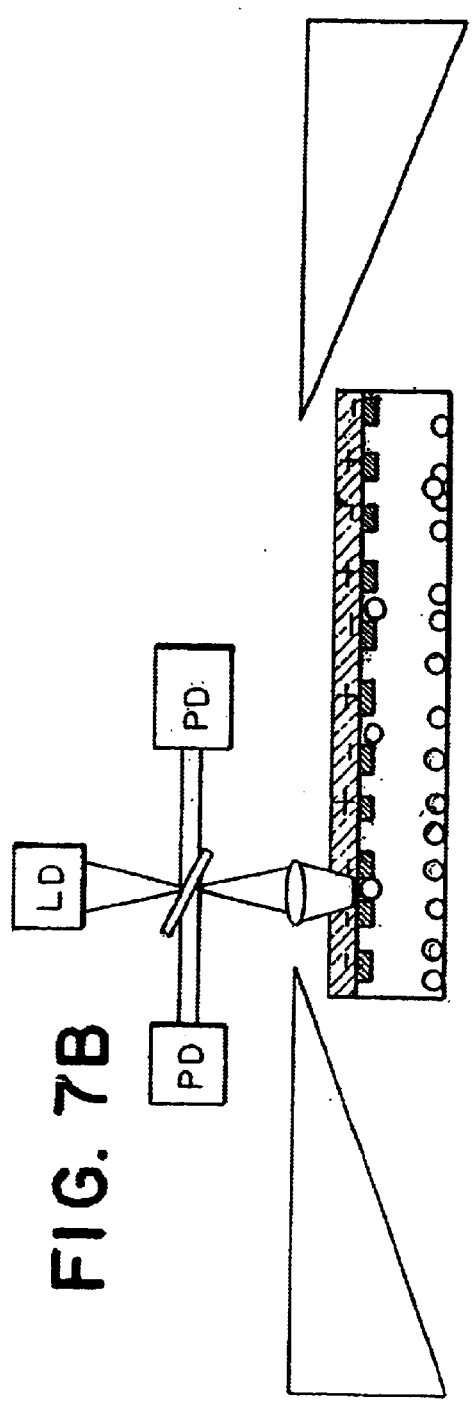
FIG. 7A
FIG. 7B

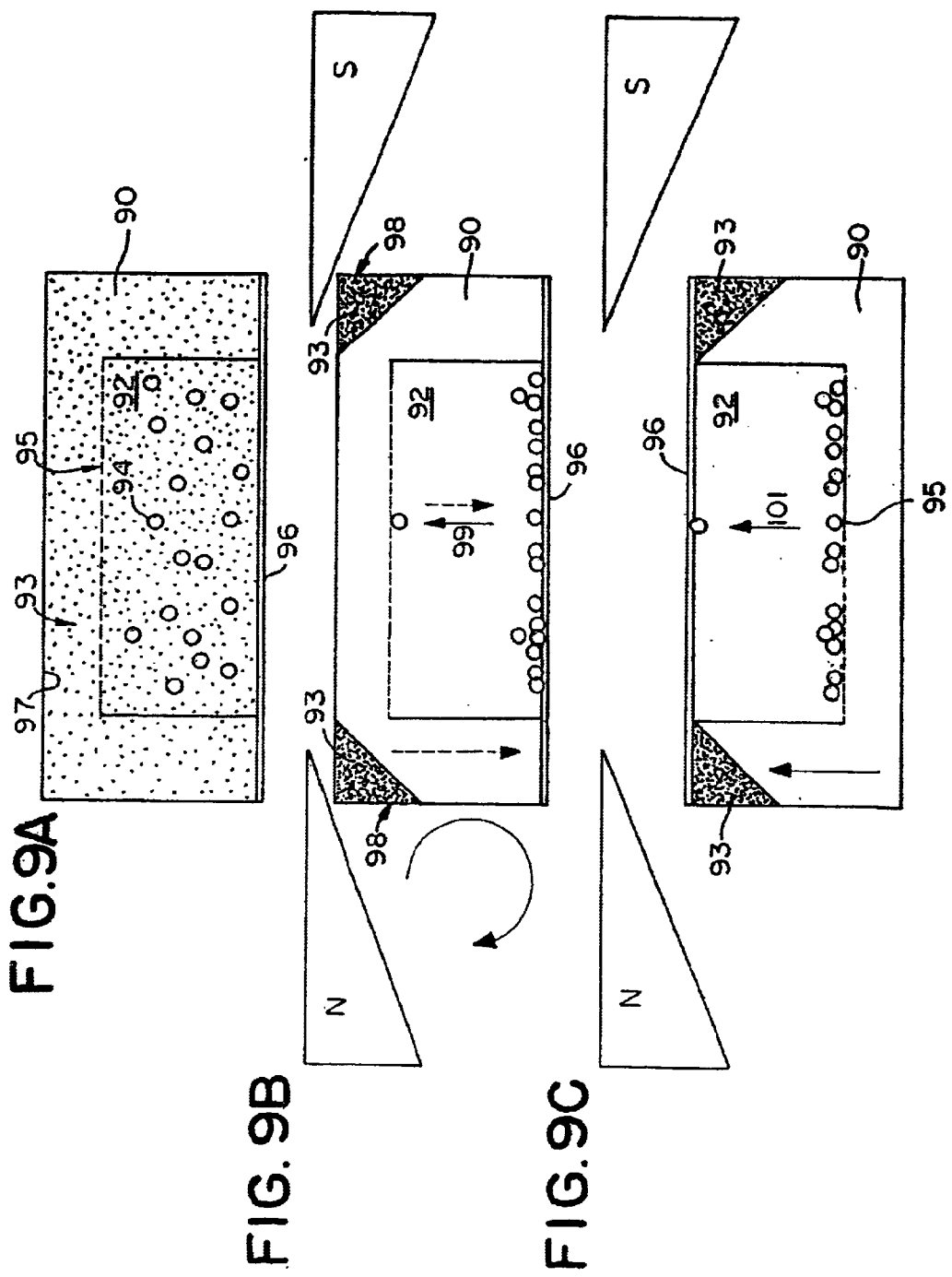

MAGNETIC SEPARATION APPARATUS AND METHODS

CROSS-REFERENCE TO RELATED APPLICATIONS

This is a division of Ser. No. 09/856,672, filed on May 24, 2001, now allowed, which is a 371 of PCT/US99/28231, filed on Nov. 30, 1999, which is a continuation-in-part of U.S. application Ser. No. 09/201,603, filed Nov. 30, 1998, now U.S. Pat. No. 6,136,182, which is a continuation-in-part of U.S. application Ser. No. 08/867,009, filed Jun. 2, 1997, now U.S. Pat. No. 5,985,153, which claims the benefit of U.S. Provisional Application No. 60/019,282, filed Jun. 7, 1996, and claims the benefit of U.S. Provisional Application No. 60/030,436, filed Nov. 5, 1996. Application Ser. No. 09/856,672, now allowed, U.S. Pat. No. 6,136,182 and U.S. Pat. No. 5,985,853 are all incorporated in full by reference herein.

BACKGROUND

The present invention relates to improved apparatus and methods for performing qualitative and quantitative analysis of microscopic biological specimens. In particular, the invention relates to such apparatus and methods for isolating, collecting, immobilizing, and/or analyzing microscopic biological specimens or substances which are susceptible to immunospecific or non-specific binding with magnetic-responsive particles having a binding agent for producing magnetically-labeled species within a fluid medium. As used herein, terms such as "target entity" shall refer to such biological specimens or substances of investigational interest which are susceptible to such magnetic labeling.

U.S. Pat. No. 5,985,853 describes an apparatus and method wherein an external magnetic gradient is employed to attract magnetically labeled target entities present in a collection chamber to one of its surfaces, and where an internal magnetic gradient is employed to obtain precise alignment of those entities on that surface. The movement of magnetically labeled biological entities to the collection surface is obtained by applying a vertical magnetic gradient to move the magnetically labeled biological entities to the collection surface. The collection surface is provided with a ferromagnetic collection structure, such as plurality of ferromagnetic lines supported on an optically transparent surface.

Once the magnetically labeled biological entities are pulled sufficiently close to the surface by the externally applied gradient, they come under the influence of an intense local gradient produced by the ferromagnetic collection structure and are immobilized at positions laterally adjacent thereto. The local gradient preferably exceeds adhesion forces which can hold the biological entities to the transparent surface after they collide with the surface. Alternatively, the adhesiveness of the surface must be sufficiently weak to allow the horizontal magnetic force to move the magnetically labeled biological entities towards the ferromagnetic structures. The smoothness and the hydrophobic or hydrophilic nature of the surface are factors that can influence the material chosen for the collection surface or the treatment of this surface to obtain a slippery surface.

In accordance with the present invention, there are described further alternative embodiments and improvements for the collection chamber, the interior geometry of the collection chamber, and further useful techniques that may be accomplished by use of a vertical magnetic gradient separator structure.

BRIEF DESCRIPTION OF THE FIGURES

FIG. 1A is a schematic diagram of a magnetic separator.

FIG. 1B is a diagram showing the magnetic field provided in the magnetic separator of FIG. 1A.

FIGS. 3A–I are plan views of alternative ferromagnetic collection structures for use in a magnetic separator.

FIGS. 7A and 7B are successive schematic diagrams sowing a method of charge-enhanced collection in a magnetic separator.

FIGS. 9A–9C are successive schematic views showing a method of particle separation in a magnetic separator.

DETAILED DESCRIPTIONS

Figure 2A:
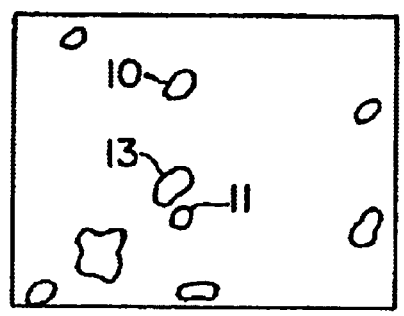
FIGS. 2A–C are microphotographs of specimens collected in a magnetic separator.

I. Vertical Gradient Collection and Observation of Target Entities

In a first embodiment of the invention, target entities such as cells are collected against a collection surface of a vessel without subsequent alignment adjacent to a ferromagnetic collection structure. The collection surface is oriented perpendicular to a magnetic field gradient produced by external magnets. In this embodiment, magnetic nanoparticles and magnetically labeled biological entities are collected in a substantially homogeneous distribution on an optically transparent surface while non-selected entities remain below in the fluid medium. This result can be accomplished by placing a chamber in a gap between two magnets arranged as shown in FIG. 1A, such that the chamber's transparent collection surface is effectively perpendicular to a vertical field gradient generated by external magnets 3. The magnets 3 have a thickness of 3 mm, and are tapered toward a gap of 3 mm. The magnets 3 are held in a yoke 1, which rests atop a housing 2. A vessel support 4 holds the vessel 6 in a region between the magnets where the lines of magnetic force are directed substantially perpendicular to the collection surface 5 of the vessel 6. The collection surface of the vessel is preferably formed of a 0.1 mm thick polycarbonate member. The collection surface is parallel to, and 2 mm below, the upper surface of the external magnets 3. The space between the inner, top surface edges of the magnets is 3 mm.

The taper angle of the magnets 3 and the width of the gap between the two magnets determine the magnitude of the applied magnetic field gradient and the preferable position of the collection surface of the vessel. The field gradient produced by the magnets can be characterized as having a substantially uniform region, wherein the gradient field lines are substantially parallel, and fringing regions, wherein the gradient field lines diverge toward the magnets. FIG. 1B shows mathematically approximated magnetic field gradient lines for such a magnet arrangement. The magnetic field lines (not shown) are predominantly parallel to the chamber surface while the gradient lines are predominantly perpendicular to it. To collect a uniformly distributed layer of the target entities, the vessel is positioned to place the chamber in the uniform region such that there are substantially no transverse magnetic gradient components which would cause lateral transport of the magnetically labeled biological entities to the collection surface.

To illustrate the collection pattern of magnetic material on the collection surface area, a chamber with inner dimensions of 2.5 mm height (z), 3 mm width (x) and 30 mm length (y) was filled with 225 µl of a solution containing 150 nm diameter magnetic beads and placed in between the magnets as illustrated in FIG. 1A. The magnetic beads moved to the collection surface and were distributed evenly. When the vessel was elevated relative to the magnets, such that a significant portion of the top of the vessel was positioned in a fringing region, significant quantities of the magnetic particles parallel toward and accumulated at respective lateral areas of the collection surface positioned nearest the magnets.

In order to enhance uniformity of collection on the collection surface, the surface material can be selected or otherwise treated to have an adhesive attraction for the collected species. In such an adhesive arrangement, horizontal drifting of the collected species due to any deviations in positioning the chamber of deviations from the desired perpendicular magnetic gradients in the "substantially uniform" region can be eliminated.

Figure 2B:
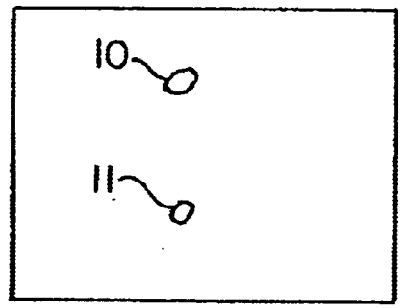
Figure 2C:
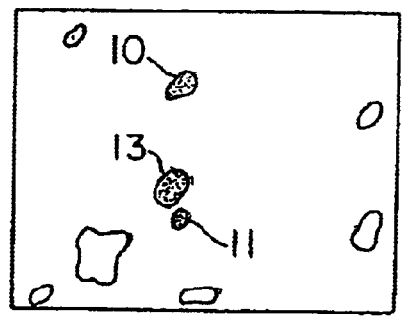

An example of the use of the present embodiment discussed device is a blood cancer test. Tumor derived epithelial cells can be detected in the peripheral blood. Although present at low densities, 1–1000 cells per 10 ml of blood, the cells can be retrieved and quantitatively analyzed from a sample of peripheral blood using an anti-epithelial cell specific ferrofluid. FIG. 3 illustrates an example of the use of the magnets and the chamber with no ferromagnetic structure on the collection surface to localize, differentiate and enumerate peripheral blood selected epithelial derived tumor cells. In this example, 5 ml of blood was incubated with 35 µg of an epithelial cell specific ferrofluid (EPCAM-FF, Immunicon Corp., Huntingdon Valley, Penn.) for 15 minutes. The sample was placed in a quadrupole magnetic separator (QMS 17, Immunicon Corp.) for 10 minutes and the blood was discarded. The vessel was taken out of the separator and the collected cells present at the wall of the separation vessel were resuspended in a 3 ml of a buffer containing a detergent to permeabilize the cells (Immunoperm, Immunicon Corp.) and placed back in the separator for 10 minutes. The buffer containing the detergent was discarded and the vessel was taken out of the separator and the cells collected at the wall were resuspended in 200 µl of a buffer containing the UV excitable nucleic acid dye DAPI (Molecular Probes) and Cytokeratin monoclonal antibodies (identifying epithelial cells) labeled with the fluorochrdme Cy3. The cells were incubated for 15 minutes after which the vessel was placed in the separator. After 5 minutes the uncollected fraction containing excess reagents was discarded, the vessel was taken out of the separator and the collected cells were resuspended in 200 µl of an isotonic buffer. This solution was placed into a collection chamber and placed in the magnetic separator shown in FIG. 1A. The ferrofluid labeled cells and the free ferrofluid particles moved immediately to the collection surface and were evenly distributed along the surface as is shown in FIG. 2A. The figure shows a representative area on the collection surface using transmitted light and a 20× objective. In FIG. 2B the same field is shown but now a filter cube is used for Cy3 excitation and emission. Two objects can be identified and are indicated with 1 and 2. FIG. 2C shows the same field but the filter cube is switched to one with an excitation and emission filter cube for DAPI. The objects at position 1 and 2 both stain with DAPI as indicated at positions 3 and 5 confirm their identity as epithelial cells. Additional non epithelial cells and other cell elements cells are identified by the DAPI stain; an example is indicated by the number 4.

II. Ferromagnetic Collection Structures Producing Central Alignment of Cells

To provide for spatially patterned collection of target entities, a ferromagnetic collection structure can be provided on the collection surface of the vessel, in order to produce an intense local magnetic gradient for immobilizing the target entities laterally adjacent to the structures. The various ferromagnetic structures described below have been made by standard lithographic techniques using Nickel (Ni) or Permalloy (Ni—Fe alloy). The thickness of the evaporated metal layers was varied between 10 nm to 1700 nm. The 10 nm structures were partially transparent. The immobilizing force of these thin structures was, however, considerably less than those in the 200–700 nm thickness range. Although immobilization and alignment of magnetically labeled biological entities occurred sufficiently reliably, use of these moderately thicker structures was facilitated by a collection surface which had no or little adhesive force. Collection structures thicknesses between 200 and 1700 nm were effective in capturing the magnetically labeled biological entities and overcoming the surface adhesion.

FIGS. 3A through 3I show various magnets for ferromagnetic collection structures.

In FIG. 3B the ferromagnetic collection structure comprises Ni wires with a spacing comparable to the cell diameter (nominally 10 microns). A decrease in the spacing between the wires shown in FIG. 3C, produces a much more uniform cell position relative to the wire edge. Almost all cells appear to be centrally aligned. However, a portion of each cell overlaps, and is obscured by the Ni wire.

Figure 4:
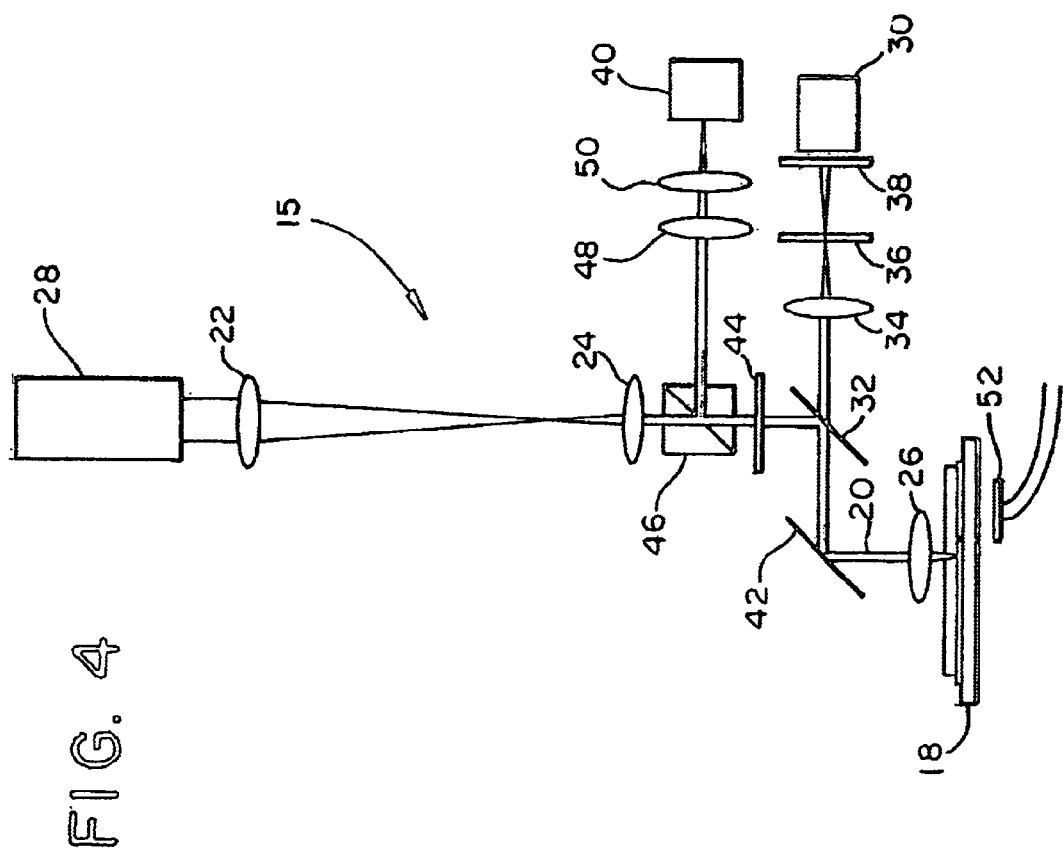
FIG. 4 is a schematic diagram of an optical tracking and detection mechanism for analyzing species collected in a magnetic separator.

Cells collected along the ferromagnetic collection structures can be detected by an automated optical tracking and detection system. The tracking and detection system, shown in FIG. 4, employs a computer controlled motorized stage to move the magnets and chamber in the X and Y directions under a laser beam having an elliptical 2–15 µm spot. The maximum speed of the table is 2 cm/sec in the Y direction, and 1 mm/sec in the X direction. Two cylindrical lenses (1) and (2) and a position adjustable objective (3) taken from a Sony Compact Disk player were used to make a 2×15 µm elliptical spot on the sample with a 635 nm laser diode (4) as a light source (see inset 5). The light reflected from the sample was projected on a photomultiplier (6) through a dichroic mirror (7), a spherical lens (8), a diaphragm (9) and band pass filters (10). Measurement of differences in the polarization direction of the light reflected from the wires and projected on a quadrant photodiode (11) through the mirror (12), the dichroic mirror (7), a quarter-wavelength plate (13), a polarized beam splitter (14), a cylindrical lens

(15) and a spherical lens (16) were used to determine the position of the laser spot on the sample and to feed back a signal to the objective (3) to correct its position for any deviations (see insert 17). A photodiode (18) was positioned perpendicular to the sample and was used to measure light scattered from the illuminated events. The feedback mechanism of the tracking system were optimized such that the laser beam kept the same X and Z position with respect to the lines while scanning in the Y direction with speeds up to 1 cm/sec. At the end of the 2 cm long line the position of the objective was changed to the next line, this was repeated until all the lines of the chamber were scanned.

Figure 5A:
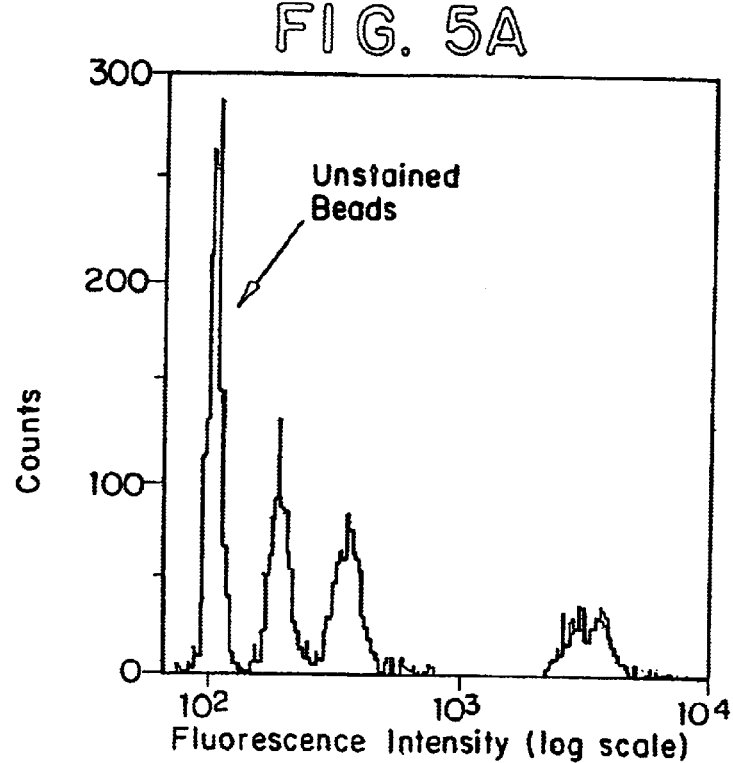
FIGS. 5A–B are histograms of fluorescence signals obtained from a magnetic separator (5A) and from a flow cytometer (5B) employed to quantify species in identical fluid samples.
Figure 5B:
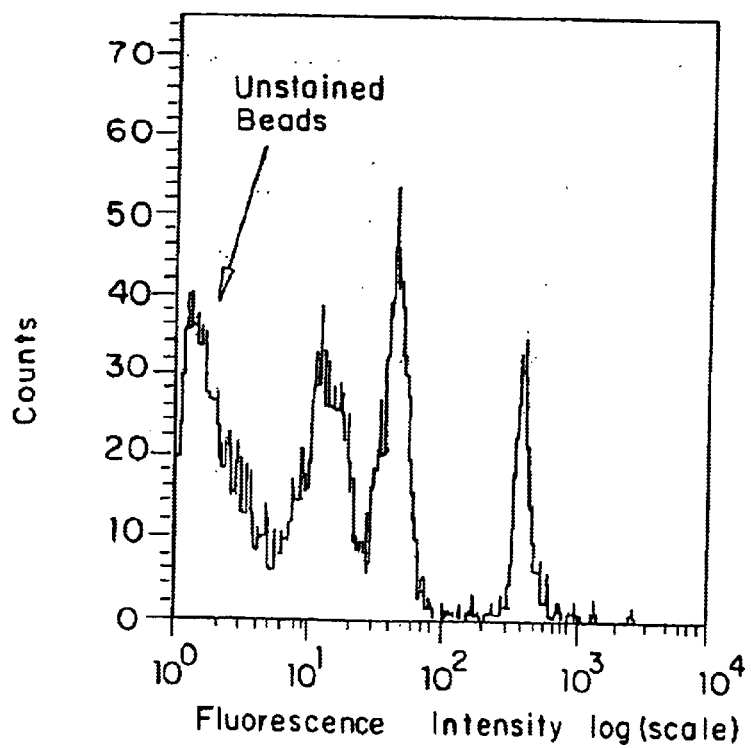

To evaluate the performance of the tracking and detection system and compare it to that of a flow cytometer, 6 $\mu$m polystyrene beads were prepared which were conjugated to ferrofluid as well as to four different amounts of the fluorochrome Cy5. The beads were used at a concentration of $10^5$ ml$^{-1}$ placed into a chamber with ferromagnetic collection structures of the type illustrated in FIG. 3C. The chamber was placed in the uniform gradient region between the two magnets and all beads aligned between the lines. The tracking and detection system was used to measure the fluorescence signals obtained while scanning along the ferromagnetic wires. FIG. 5A shows a histogram of the fluorescence signals of the bead mixture. Four clearly resolved peaks are discernible representing the beads with no Cy5, dimly, intermediate and brightly labeled with Cy5. A mixture of the same beads was made and measured with a flow cytometer also equipped with a 635 nm laser diode (FACScalibur, BDIS, San Jose Calif.). The histogram of the fluorescence signals is shown in FIG. 5B and shows that although four different populations were discernible, they are clearly less resolved than in case samples, measured with the magnetic immobilization cytometer of the present invention. These results demonstrate that the alignment of the beads obtained with the system described herein provides a sensitivity and accuracy of the measurement of fluorescent beads which is superior to that of the flow cytometer.

In applications where it is desired to simultaneously measure biological entities with significant differences in size, the collection structure can be configured to have a non-uniform geometry in order to centrally-align cells or other species of differing sizes. An example of such a structure is shown in FIG. 3D. A collection structure pattern was made with one area of the collection surface having wires with a period of 10 $\mu$m and a spacing of 7 $\mu$m, and another area having wires with a period of 25 $\mu$m and a spacing of 7 $\mu$m. This was used to collect both the small platelets and the larger leukocytes from whole blood. Before collection, the blood was incubated with ferrofluid specific for platelets and leukocytes from whole blood. Before collection, the blood was incubated with ferrofluids specific for platelets and leukocytes i.e. a ferrofluid labeled with the monoclonal CD41 and a ferrofluid labeled with the monoclonal antibody CD45 respectively. The leukocytes and platelets align along the wires in the respective areas of the collection surface as is illustrated in FIG. 3D. The measurement of the platelets can be performed at the area with the small spaces between the wires and the measurement of the leukocytes can be performed at the area with the larger spaces between the wires. The variation of gap width along the length of the ferromagnetic structure provides linear alignment of the collected cells of different sizes along a common central axis.

Many more collection structure patterns are possible within the scope of the invention for capturing and centrally aligning cells of varying sizes in a single sample. Four examples are illustrated in FIGS. 3E, 3F, 3G, 3H and 3I. FIG. 3E shows a similar wire spacing as shown in FIG. 3C, but the wires have lateral protrusions formed along the lengths thereof. For the geometry of FIG. 3E, there were two positions chosen by the cells—to the left or right of the protrusions as shown. Such a design induces a periodic positioning of the cells in both axes of the collection plane. Adding an asymmetric triangular "prong" edge shape instead of a "bar," as illustrated in FIG. 3F removes the slight (right-left) asymmetry observed in the FIG. 3E. Adding a larger asymmetric triangular "prong" edge shape as is illustrated in FIG. 3G is also effective for cells of varying sizes. A sharper triangular style is illustrated in FIG. 3H. FIG. 3I shows an array of isolated rectangles, with their spacing along one axis set to match the cell size. The spacing along the other axis exceeds the cell size, so that cells move freely toward the positions between more closely-spaced sides of the rectangles.

Figure 6A:
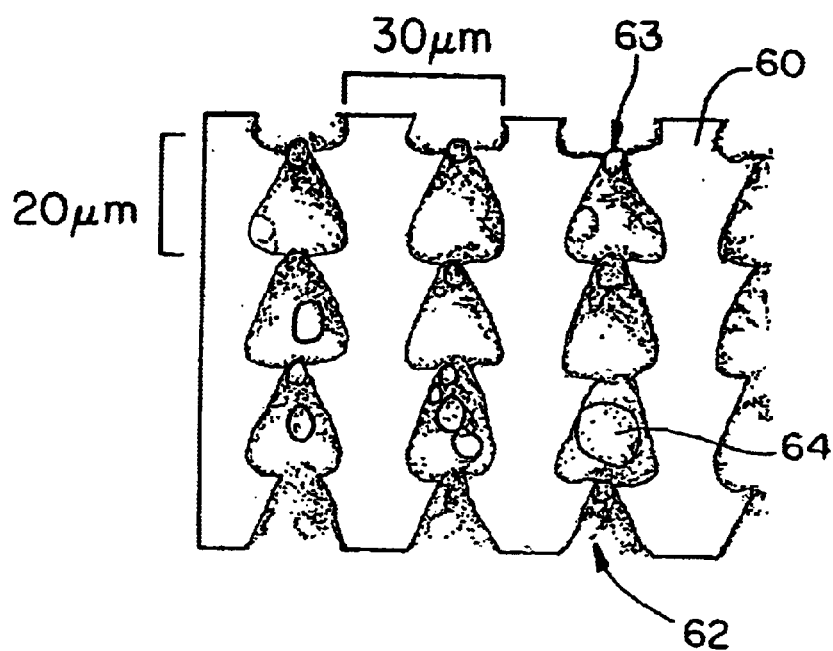
FIGS. 6A–6B are microphotographs of specimens collected in a magnetic separator.
Figure 6B:
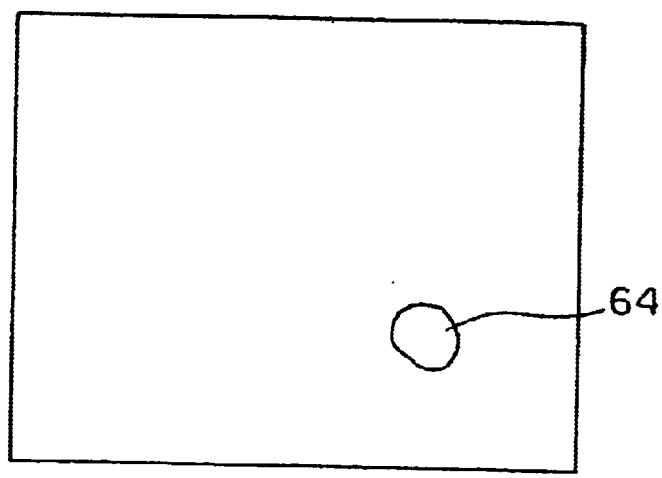

An example of the utilization of custom designed ferromagnetic structure on the collection surface is a blood cancer test. Tumor derived epithelial cells can be detected in the peripheral blood and can be retrieved quantitatively from peripheral blood using anti-epithelial cell specific ferrofluids. The physical appearance of the tumor derived epithelial cells is extremely heterogeneous ranging from 2–5 $\mu$m size apoptotic cells to tumor cell clumps of 100 $\mu$m size or more. To accommodate this large range of sizes, triangular shaped ferromagnetic structures as schematically illustrated in FIGS. 3G or 3H can be used. An example of the positioning of peripheral blood derived cancer cells is illustrated in FIG. 6. In this example, 5 ml of blood was incubated with epithelial cell specific ferrofluid (EPCAM-FF, Immunicon Corp.) and processed using the same method as described above. The final cell suspension was placed in the magnetic separator. The ferrofluid labeled cells and the free ferrofluid move immediately to the collection surface. FIG. 6A shows an area on the collection surface using transmitted light and a 20× objective. The ferromagnetic collection structure is indicated with 1, the open wide collection space with 2, the narrow collection space with 3 and a large object with 4. FIG. 6B shows the same area only now UV excitation is used. The large object indeed is a large cell as confirmed by the staining with the nuclear dye indicator 5 and is nicely aligned. The tracking system described in FIG. 4 was successfully used to scan along the ferromagnetic structures illustrated in FIGS. 3H and 6A.

III. Addressable Ferromagnetic Collection Structures

Figure 8A:
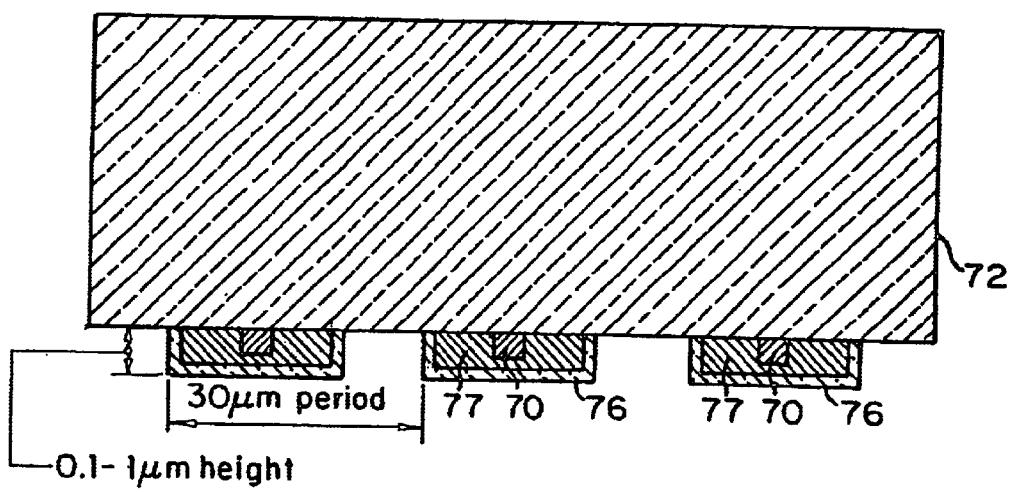
FIGS. 8A and 8B are respective cross-sectional and plan views of a combined ferromagnetic and electrically conductive collection structure for a magnetic separator.
Figure 8B:
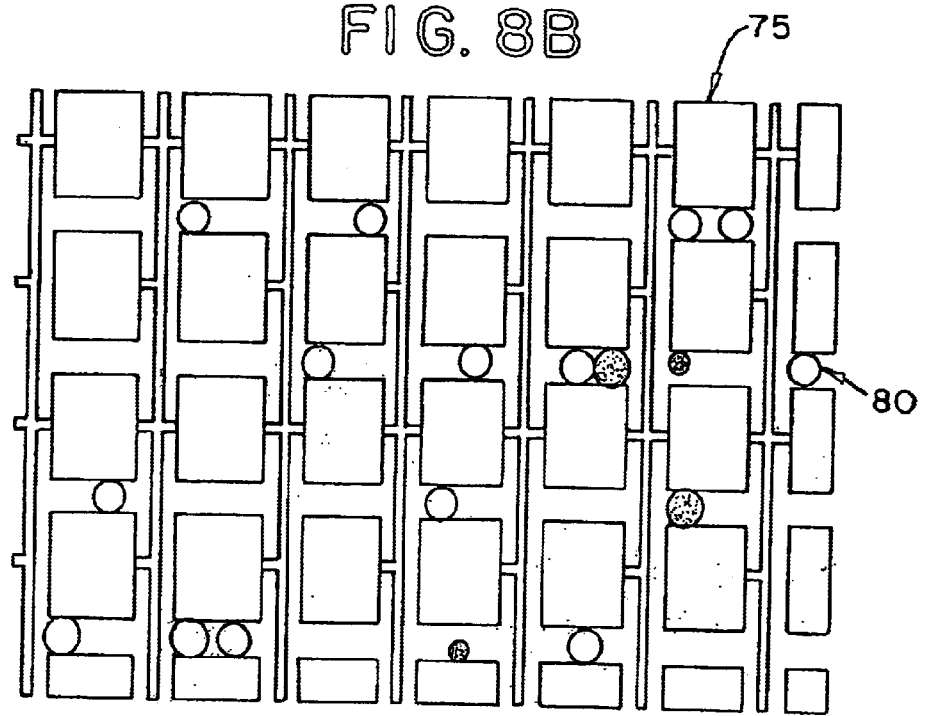

In addition to using ferromagnetic structures to create high local magnetic gradients, they also can serve as electronic conductors to apply local electronic field charges. Furthermore, electronic conductors can be formed on the collection surface to allow electronic manipulation of the collected target entities. The ability to first move biological entities to a specific location followed by an optical analysis is schematically illustrated in FIG. 7A. Subsequent application of general or localized electronic charges, shown in FIG. 7B adds another dimension to the utility of the described system. Useful applications of local electronic charges for applications involving cells, RNA, protein and DNA are known. A schematic drawing of one design of such a collection surface is illustrated in FIG. 8. To optimize the control over the electronic charge one can first evaporate a specific pattern/layers of Aluminum 1 onto an optically transparent substrate 4, which provides an electronic circuit to the individual ferromagnetic structures, 5 in FIG. 8B. The next layer of Ni or other ferromagnetic material is evaporated onto the substrate, 2 in FIG. 8A, to create the individual ferromagnetic structures 5 in FIG. 8B. An insulating layer 3 can be obtained by the evaporation of $SiO_2$ or other insulating material. Magnetically labeled biological entities 7 localize in between the ferromagnetic structures. Electronic charge can then be applied to improve the specificity of the immunospecific binding, change the orientation of the captured biological entity according to its electronic polarity, or to modify the entity properties (for example, to "explode" it) by applying an electronic charge to the conductors. The biological entities can be studied before and/or after application of electronic charges.

IV. Porous Chamber Surfaces for Excess Particle Removal

When large initial volumes of fluid samples are processed and reduced to smaller volumes by magnetic separation, the concentration of the nanometer sized (<200 nm) magnetic labeling particles increases proportionally. The collection surface in the chambers has a limited capacity for capturing unbound excess magnetic particles, and these particles may interfere with the positioning and observation of the magnetically labeled biological entities. An arrangement for separating unbound excess magnetic labeling particles form the magnetic labeled biological entities is illustrated in FIG. 9. The collection chamber comprises an outer compartment 1 and an inner compartment 2. The fluid sample containing unbound magnetic particles 3 and magnetically labeled and non-labeled biological entities 4 is placed in the inner compartment 2. At least one surface 5 of the inner chamber is porous, for example, a filter membrane having a pore size between 0.5 and 2 µm. Magnetic nanoparticles can pass through the pores, but the larger magnetically labeled cells cannot. The opposite surface of the inner chamber 6 consists of a transparent surface with or without ferromagnetic collection structures as described above.

After the inner chamber is filled with the fluid sample, the outer chamber is filled with a buffer. The vessel is then placed between the two magnets as shown in FIG. 9B. The chamber is positioned so that respective lateral portions of the vessel extend into the fringing magnetic gradient region. The unbound magnetic particles are transported by the magnetic gradient through the membrane (5) and toward respective lateral regions 8 of the outer chamber (1). This movement is consistent with the magnetic gradient field lines shown in FIG. 1B. The lateral accumulation of the particles is effectively aided by the horizontal movement of those nanoparticles which first hit the surface and then slide along the slippery surface (7).

Magnetically labeled biological entities such as cells also move according to the gradient lines (9) until they reach the membrane, whereas non magnetic biological entities settle to the bottom under the influence of gravity. After the separation of unbound particles is complete, the chamber is taken out of the magnetic separator and inverted (10). The chamber is repositioned in the uniform gradient region to optimize the homogeneity of the distribution of the cells at the collection surface, FIG. 9C. The magnetically labeled cells move towards the optically transparent surface (6) (indicated with 11 in FIG. 9B and 14 in FIG. 9C) whereas the non magnetic biological entities settle to the membrane (5) under the influence of gravity. The free magnetic nanoparticles move vertically toward the surface 6. The free magnetic nanoparticles are no longer present in the observation path and the magnetically labeled biological entities can be examined. The system described above is especially suitable for applications in which the target cell number is low, in order to avoid clogging the membrane.

V. Longitudinal Variation of Chamber Height

Figure 10A:
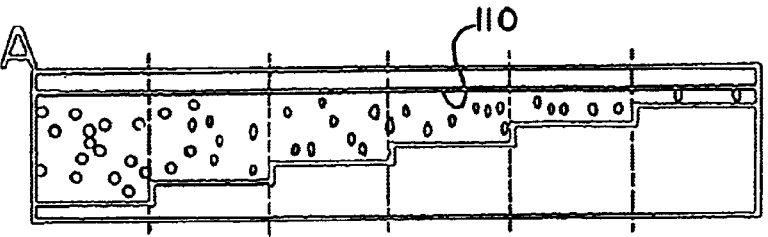
FIGS. 10A and 10B are successive schematic views showing a method of measuring particle density in a fluid having an unknown particle density.
Figure 10B:
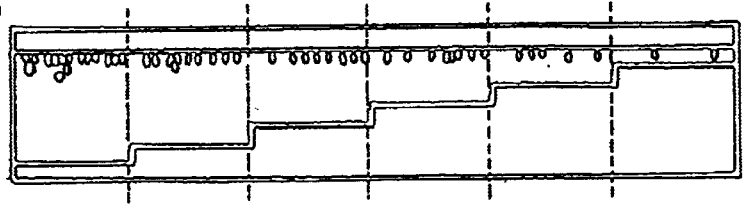
Figure 10C:
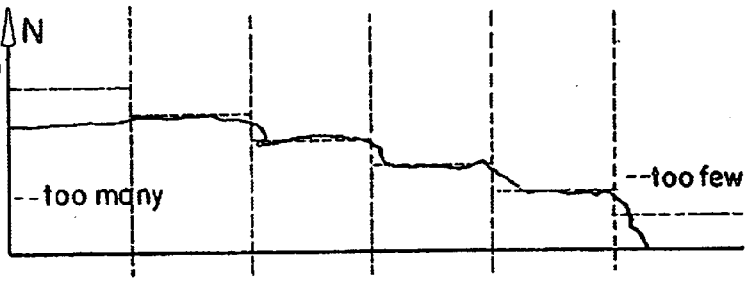

The height of the chamber in concert with the concentration of the target entity determines the density of the distribution of target entities collected at the collection surface of a vessel such as described above. To increase the range of surface collection densities which are acceptable for accurate counting and analysis, one can vary the height of the chamber to eliminate the need to dilute or concentrate the sample, for analysis of samples where the concentration may vary widely. In FIG. 10A, a cross section of a chamber is shown with a collection surface 1, and six compartments having different heights. Target cells are randomly positioned in the chamber. In FIG. 10B the same cross section is shown but now the cells have moved to the collection surface under the influence of the magnetic gradient. In the area of the highest chamber depth, the density of the cells is too high to be accurately measured, whereas in the area of the lowest chamber depth, too few cells are present to provide an accurate cell count. To further illustrate this principle, a histogram of the cell density along the collection surface is shown in FIG. 11C. Note that the number of cells in the area with the highest density is underestimated. The approach described here increases the range of concentrations which can be accurately measured as compared to the cell number measurements traditionally used in hematology analyzers and flow cytometers.

VI. Different Compartments in the Chamber

Figure 11A:
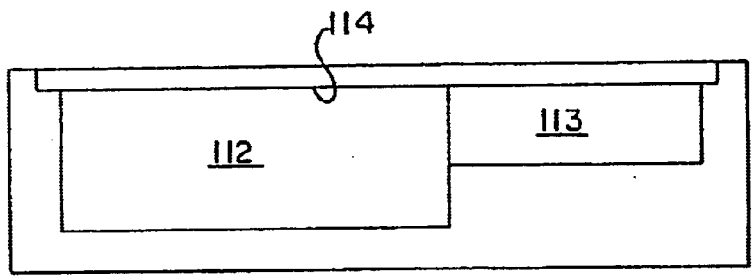
FIGS. 11A and 11B are sectional views of a separation vessel configured for multiple simultaneous analysis of fluids containing multiple target species at differing concentrations.
Figure 11B:
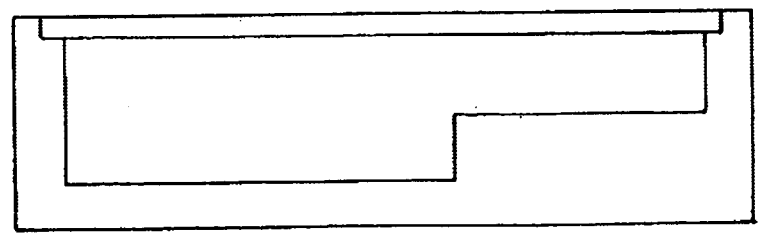

Different types of target entities present at different densities can be present in the sample. To permit simultaneous multiple analyses, chambers can be made with multiple compartments. An example of such a chamber is illustrated in FIG. 11A. The collection surface 1 and two separate compartments 2 and 3 in these chambers permit the usage of a different set of reagents. In case areas in the chamber are not separated by a wall, as illustrated with 4 in FIG. 11B, the reagents used will move all magnetically labeled cell types to the top. An example is for instance the simultaneous use of a leukocyte specific and a platelet specific ferrofluid. The density of the platelets is considerably larger than that of the leukocytes, measurement of the platelets would thus be done in the shallow part of the chamber (which may have a relatively small line spacing on the collection surface) and measurement of the leukocytes would be performed in the deeper part of the chamber (which may have a relatively larger line spacing on the collection surface; such as the arrangement shown in FIG. 3D.)

The terms and expressions which have been employed are used as terms of description and not of limitation. There is no intention in the use of such terms and expressions of excluding any equivalents of the features shown and described or any portions thereof. It is recognized, therefore, that various modifications are possible within the scope of the invention as claimed.

What is claimed is:

1. A method for optically analyzing microbiological specimens suspended in a fluid medium, comprising the steps of:
   a. magnetically labeling the microbiological specimens;
   b. containing the fluid medium in a vessel having a chamber therein for receiving the fluid medium, and having a transparent top member;
   c. positioning the vessel into a magnetic field having a substantially uniform region of vertically-directed magnetic gradient, such that the chamber is located in the uniform region;

d. collecting a uniformly-distributed layer of the magnetically labeled microbiological specimens on the interior surface of the chamber bounded by the transparent member; and e. conducting optical analysis of the magnetically-labeled microbiological specimens while maintaining the magnetically-labeled microbiological specimens collected on the interior surface of the chamber bounded by the transparent member.

2. The method of claim 1, wherein the step of the positioning the vessel comprises positioning the vessel in a gap between a pair of magnets having respective tapered surfaces facing the gap, and wherein the step of conducting optical analysis comprises microscopic observation of the magnetically-labeled microbiological specimens along an observation path extending vertically into the gap between the magnets and into the chamber.

3. The method of claim 1, comprising the step of providing for adhesion between the magnetically-labeled microbiological specimens and the interior surface of the chamber bounded by the transparent member, in order to inhibit horizontal movement of the magnetically-labeled microbiological specimens collected thereon.

4. A method of collecting and observing microbiological specimens in a fluid medium, comprising:

a. magnetically labeling the specimens by contacting the specimens with a plurality of magnetic labeling particles;

b. placing the fluid medium into a vessel having a chamber with a transparent surface and a porous wall;

c. applying a magnetic field gradient to the chamber to remove excess magnetic labeling particles through the porous wall of the chamber while retaining the magnetically labeled specimens; and d. attracting the magnetically labeled specimens toward the transparent wall for observation after removal of the excess magnetic labeling particles.

5. A method for optically analyzing microbiological specimens suspended in a fluid medium, comprising the steps of:

a. magnetically labeling the microbiological specimens;

b. containing the fluid medium in a vessel having a chamber therein for receiving the fluid medium, a transparent top member, and the chamber having two collection regions of differing heights;

c. positioning the vessel into a magnetic field having a substantially uniform region of vertically directed magnetic gradient, such that the chamber is located in the uniform region; and d. collecting the magnetically labeled microbiological specimens on respective regions of the interior surface of the transparent top member corresponding to the collection regions of the chamber.

6. The method of claim 5 comprising the step of providing a barrier between the collection regions of the chamber.

* * * * *